US009435745B2

(12) United States Patent
Jaracz et al.

(10) Patent No.: US 9,435,745 B2
(45) Date of Patent: *Sep. 6, 2016

(54) MEASURING THE RATE OF RELEASE OF METAL IONS

(71) Applicant: Colgate-Palmolive Company, Piscataway, NJ (US)

(72) Inventors: Stanislav Jaracz, Somerset, NJ (US); Ravi Subramanyam, Belle Mead, NJ (US); Michael Prencipe, Princeton Junction, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/580,510

(22) Filed: Dec. 23, 2014

(65) Prior Publication Data

US 2016/0178527 A1    Jun. 23, 2016

(51) Int. Cl.

| G01N 21/78 | (2006.01) |
|---|---|
| G01N 33/20 | (2006.01) |
| G01N 21/79 | (2006.01) |
| G01N 21/77 | (2006.01) |
| A61Q 11/00 | (2006.01) |

(52) U.S. Cl.
CPC .............. *G01N 21/78* (2013.01); *G01N 21/77* (2013.01); *G01N 21/79* (2013.01); *A61Q 11/00* (2013.01); *G01N 33/20* (2013.01)

(58) Field of Classification Search
CPC ...... G01N 33/20; G01N 21/77; G01N 21/78; G01N 21/79; Y10T 436/17; Y10T 436/18; Y10T 436/20; Y10T 436/200833; Y10T 436/203332; Y10T 436/25125; A61Q 11/00
USPC ....... 436/34, 73, 77, 81, 106, 119, 127, 128, 436/131, 164, 166, 175; 422/400, 82.05; 424/49
See application file for complete search history.

(56) References Cited

U.S. PATENT DOCUMENTS

| 4,289,754 | A | | 9/1981 | Dhabhar et al. | |
|---|---|---|---|---|---|
| 4,992,259 | A | | 2/1991 | Schiraldi et al. | |
| 5,221,626 | A | * | 6/1993 | Yamazato | G01N 31/22 436/166 |
| 5,330,748 | A | | 7/1994 | Winston et al. | |
| 6,159,459 | A | | 12/2000 | Hunter et al. | |
| 6,821,786 | B2 | * | 11/2004 | Rupp | G01N 33/84 422/423 |
| 2003/0215522 | A1 | * | 11/2003 | Johnson | A61K 8/27 424/642 |
| 2004/0001897 | A1 | | 1/2004 | Amano et al. | |
| 2007/0292900 | A1 | * | 12/2007 | Frederickson | G01N 33/57434 435/7.23 |
| 2010/0099195 | A1 | * | 4/2010 | Frederickson | G01N 33/84 436/81 |
| 2014/0024010 | A1 | | 1/2014 | Akashi et al. | |

FOREIGN PATENT DOCUMENTS

| WO | WO0172347 | 4/2001 |
|---|---|---|
| WO | WO03/088957 | 10/2003 |
| WO | WO2007/013937 | 2/2007 |
| WO | WO2008/041055 | 4/2008 |
| WO | WO2011028878 | 3/2011 |
| WO | WO2011108300 | 9/2011 |
| WO | WO 2011/016984 | 10/2011 |

OTHER PUBLICATIONS

Anonymous, "Fluorescent Indicators for Zn2+ and other metal ions", The Molecular Probes Handbook, Life Technologies Inc, http://www.lifetechnologies.com/uk/en/home/references/molecular-probes-the-handbook/indicators-for-ca2-mg2-zn2-and-other-metal-ions/fluorescent-indicators-for-zn2-and-other-metal-ions.html accessed Nov. 13, 2014.

Anonymous, Standard Electrode Potential (data page), http://en.wikipedia.org/wiki/Standard_electrode_potential_(data_page), accessed Nov. 13, 2014.

Areco et al.,, 2007, "Zinc Biosorption by Seaweed Illustrated by the Zincon Colorimetric Method and the Langmuir Isotherm", Journal of Chemical Education, vol. 84, No. 3, pp. 302-305.

Brading et al., 2009, "Gum health benefits of a silica based fluoride toothpaste containing zinc citrate, potassium citrate, hydroxyapatite and vitamin E acetate", International Dental Journal, 59, pp. 332-337.

Brophy et al., 2012, "Calcium ion gradients modulate the zinc affinity and antibacterial activity of human calprotectin", J Am Chem Soc, 134, 43, pp. 18089-18100.

Chen et al., 2001, "Catalytic selenols couple the redox cycles of metallothionein and glutathione", European Journal of Biochemistry, 268, 3346-3353.

Clever et al., 1992, "The Solubility of Some Sparingly Soluble Salts of Zinc and Cadmium in Water and in Aqueous Electrolyte Solutions", J Phys Chem Ref Data, 21, 5, pp. 941-966.

Ejnik et al., 2010, "Mechanism of Cadmium Ion Substitution in Mammalian Zinc Metallothionein and Metallothionein Alpha Domain; Kinetic and Structural Studies", Inorg. Chem., 49, pp. 6525-6534.

Gulson et al., 2010, "Small amounts of zinc from zinc oxide particles in sunscreens applied outdoors are absorbed through human skin", Toxicological Sciences, 118, 1, pp. 140-149.

Harrap et al., 1984, "Human oral retention of zinc from mouthwashes containing zinc salts and its relevance to dental plaque control", Archs Oral Biol, 29, 2, pp. 87-91.

(Continued)

*Primary Examiner* — Maureen Wallenhorst

(57) ABSTRACT

A method of measuring the relative rates of release of a target metal ion from two or more samples includes: (i) providing at least two aliquots of a solution including an indicator, the indicator having a color; (ii) dispersing a sample into each aliquot; and (iii) during step (ii), monitoring the color of the indicator in situ to determine the rates of release of the target metal ions from the samples relative to one another. Each sample includes at least one source of the target metal ion. The indicator contains zincon. The samples are oral care compositions selected from a toothpaste, a tooth gel, and a tooth powder. The target metal ion is selected from the stannous and zinc (II).

10 Claims, No Drawings

(56) References Cited

OTHER PUBLICATIONS

He et al., 2002, "Inhibitory effect of ZnCl2 on glycolysis in human oral microbes", Archs Oral Biol, 47, 2, pp. 117-129.

Klemm, 2011, "Microclectrochemical characterization of Zn, ZnO and Zn—Mg alloys with online dissolution monitoring", Ruhr University Bochum, Germany.

Mabrouk et al., 1992, "Direct electrochemical synthesis of cobalt, nickel, copper, zinc, cadmium, tin and lead complex", Trans Met Chem, 17, pp. 1-4.

Mitra et al., 1960, "The reaction between polyvalent metal cations and alkali metal pyrophosphates" Proc Nat Inst Sci India, 26A, pp. 151-161.

Morozova et al., 1976, Zn2P2O7—K4P2O7—H2O System at 25°, . J Inorg Chem, 12(6):878.

Nevitt et al., 1958, "Topical applications of sodium fluoride and stannous fluoride", Public Health Rep, vol. 73, No. 9, pp. 847-850.

Ozedimir et al., 1998, "The Determination of Salivaiy Zinc Level Following Delivery from Zinc Containing Toothpaste", Tr. J. of Medical Sciences, 28, pp. 281-283.

Rakhmatullina et al., 2013, "Inhibition of enamel erosion by stannous and fluoride containing rinsing solutions", Schweiz Monatsschr Zahnmed, vol. 123, pp. 192-197.

Richter et al., 2002, "Solid phase spectrophotometric determination of copper in water by using immobilized zincon in a sephadex A25 resin", Anal. Lett. 35, pp. 635-646.

Skog et al., 1964, "A comparative investigation of the percutaneous absorption of metal compounds in the guinea pig by means of radioactive isotopes: 51Cr, 58Co, 65Zn, 110mAg, 115mCd, 203Hg", J Invest Dermatol, 43, 3, pp. 187-192.

Thompson, 1989, "Chapter 22: Zinc Links: Coordination Chemistry and Nutritional Deficiency" in "Chemtrek Small Scale Experiments for General Chemistry", Prentice Hall, NJ, USA.

Wilcox, 2009, "The black and white of immersion tin: keeping an eye on cupric ions can eliminate black tin", Printed Circuit Design & Fab, Jul. 1, 2009.

Yoe et al., 1952, "A new colorimetric reagent for zinc", Anal. Chim. Acta, vol. 6, pp. 526-527.

Zhang, et al., 2009. "Effect of resveratrol and zinc on intracellular zinc status in normal human prostate epithelial cells", Am J Physiol Cell Physiol, 297, C632-C644.

\* cited by examiner

MEASURING THE RATE OF RELEASE OF METAL IONS

TECHNICAL FIELD

The present invention generally relates to methods for measuring the rate of release of metal ions from an oral care composition, and to the use of an indicator to measure the rate of release of metal ions from an oral care composition.

BACKGROUND

Oral care compositions, such as toothpastes, may comprise metal ions as active ingredients. Zinc (II) ions and stannous (tin (II)) ions are perhaps the most important active metal ions. Stannous ions ($Sn^{2+}$) are used in oral care compositions because they display biocidal activity and are effective in preventing dental erosion (Raklnatullina et al, 2013. "Inhibition of enamel erosion by stannous and fluoride containing rinsing solutions", Schweiz Monatsschr Zahnmed, vol. 123, pp. 192-197). Zinc ions similarly display antibacterial properties.

In order to provide therapeutic activity, the metal ions must be released from the oral care composition into the oral cavity. Oral care compositions are typically contacted with the oral cavity for only a brief period before being rinsed away. The delivered dosage of metal ions is therefore dependent upon their rate of release from the composition. This must be taken into account when formulating oral care compositions. Accordingly, there is a need in the an for methods for measuring the rate of release of zinc and stannous ions from oral care compositions.

In addition, aqueous solutions comprising stannous ions have been reported to be unstable (Nevin el al, 1958. "Topical applications of sodium fluoride and stannous fluoride", Public Health Rep, vol. 73, no 9, pp. 847-850). This is believed to he the result of oxidation of the stannous ions to inactive stannic (tin (IV)) ions. There is therefore a need for methods of measuring the rate of oxidation of stannous ions.

BRIEF SUMMARY

In one aspect, the present invention provides a method of measuring the relative rates of release of a target metal ion from two or more samples, each sample comprising at least one source of the target metal ion, which method comprises: (i) providing at least two aliquots of a solution including an indicator, the indicator having a colour; (ii) dispersing each sample into one of the aliquots; and (iii) during step (ii), monitoring the colour of the indicator in situ to determine the rates of release of the target metal ion from the samples relative to one another; wherein the indicator comprises zincon; wherein each sample is an oral care composition selected from a toothpaste, a tooth gel, and a tooth powder; and wherein the target metal ion is selected from stannous and zinc (II). It has surprisingly been found that, by monitoring the colour of the zincon indicator while the oral care compositions are being dispersed into the aliquots, the relative rates of release of zinc ions or stannous ions from the sample may be compared. As used herein, the term "in situ" means that the colour is monitored using indicator which is in contact with the oral care composition, i.e. without the removal and/or filtration of aliquots of the solution. The method allows for the cost-effective measurement of the rate of release of metal ions from an oral care composition. The method is useful in the formulation of oral care compositions because it allows the rapid comparison of the rate of release of metal ions from candidate oral care compositions. Other applications of the method include the testing of existing oral care compositions, for example for quality control or quality assurance purposes.

The method is useful for comparing the relative rates of release of metal ions from two or more samples. The samples may be dispersed into the aliquots at the same time. This allows the direct side-by-side comparison of the samples. Alternatively, the samples may be tested at different times. In this arrangement, step (iii) preferably includes recording a video of the aliquots.

The solution may have a pH in the range of 7 to 10, and preferably has a $^{pH}$ in the range of 9 to 9.5. Zincon has acidic functional groups and therefore dissolves easily under alkaline conditions in the anionic form. Adjusting the pH of the solution to provide anionic. ARCM facilitates the reaction between the zincon and the positively-charged metal ions, increasing the rate of the reaction and thus improving detection of the rate of release of the ions.

The solution may comprise a buffer. Buffers are useful for maintaining the pH of the solution within a desired range. For example, the pH may be selected to maximise the rate of reaction between the target metal ions and the zincon. When the target metal ion is zinc (II), the buffer preferably does not comprise a chelating agent, because zincon binds relatively weakly to zinc (II). The amount of the zincon present in the solution is not particularly limited. The zincon may be present in the solution in an amount in the range of 10 to 100 ppm. The use of a dilute zincon solution improves the sensitivity of the method, because a smaller amount of the target metal ion is required to produce a visible colour change.

The method may be used to test two or more samples simultaneously. In this arrangement, step (i) comprises providing at least two aliquots of the solution; and step (ii) comprises dispersing a sample into each aliquot. Testing two or more samples at the same time allows the direct comparison of the release of metal ions from each sample.

Step (iii) of the method may comprise recording a video of the solution. This allows a direct comparison to be made with subsequent samples.

The target metal ion may be stannous. In this arrangement, the sample may further comprise a source of zinc ions. Zincon has been found to react with stannous ions in preference to zinc ions. The rate of release of stannous ions may therefore be detected even in the presence of zinc ions.

In the arrangements where the target metal ion is stannous, step (ii) may comprise agitating the solution in the presence of oxygen, the agitation being intermittent so as to allow oxidation of stannous ions to be detected using the indicator. For some applications, it may be useful to measure the rate of oxidation of stannous ions to stannic ions. While stannous ions are beneficial for oral health, stannic ions are not believed to display any useful therapeutic activity. It is therefore useful to establish whether or not stannous ions remain in solution after they are released from the oral care composition.

The target metal ion may be zinc (II). In this arrangement, when the sample comprises a source of stannous ions the solution comprises an oxidising agent for oxidising the stannous ions to stannic ions. It has been found that no colour change occurs when stannic ions are contacted with zincon, and that the presence of stannic ions does not interfere with the detection of zinc ions. Therefore, by oxidising stannous ions to stannic ions, zinc may be detected. Alternatively, zinc may be detected in the presence of stannous by increasing the concentration of the indicator. The reaction between zincon and zinc produces a blue complex, whereas the reaction with stannous produces a colourless complex. If a sufficiently high concentration of indicator is used, that is, if the zincon concentration exceeds the stannous concentration, the presence of zinc may therefore be detected in the presence of stannous.

The nature of the oxidising agent is not particularly limited. The preferred oxidising agent is hydrogen peroxide. Hydrogen peroxide reacts rapidly with stannous ions and is readily commercially available.

In another aspect, the present invention provides the use of an indicator to measure the relative rates of release of a target metal ion from two or more oral care compositions into a solution, wherein the target metal ion is selected from stannous and zinc (II), wherein the oral care composition is selected from a toothpaste, a tooth gel, and a tooth powder and wherein the indicator comprises zincon. As noted above, measuring the relative rates of release of metal ions is useful during the development of new oral care compositions and also finds applications in the testing of existing oral care compositions, for example for quality control or quality assurance.

The target metal ion may be zinc (II). In this arrangement, when the oral care composition comprises a source of stannous ions, the solution preferably comprises an oxidising agent.

In another arrangement, the target metal ion may be stannous. In this arrangement, the indicator may be used to detect the rate of oxidation of the stannous ions.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiments is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

As used herein, the term "zincon" refers to o-[α-(2-hydroxy-5-sulfophenyl azo)-benzylidene hydrazine] benzoic acid, which has CAS number 56484-13-0. The structure of the sodium salt of zincon is shown below:

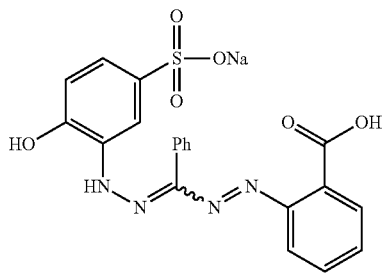

Zincon is a coloured dye which appears to be red in aqueous solution. Contacting zincon with zinc (II) ions results in the formation of a blue complex. The use of zincon as an indicator for zinc has been described previously (Yoe and Rush, 1952, "A new colorimetric reagent for zinc", Anal. Chim. Acta, vol. 6, pp 526-527). Outside the field of oral care, zincon has been used to investigate the kinetics of a reaction between the protein metallothionein and cadmium (ii) ions in a solution (Ejnik et al, 2010. "Mechanism of Cadmium Ion Substitution in Mammalian Zinc Metallothionein and Metallothionein Alpha Domain; Kinetic and Structural Studies", Inorg. Chem., 49, pp. 6525-6534). Zincon has also been used to investigate the biosoiption of zinc by seaweed (Areco et al, 2007. "Zinc Biosorption by Seaweed Illustrated by the Zincon Colorimetric Method and the Langmuir Isotherm", Journal of Chemical Education, Vol. 84, No. 3, pp. 302-305). In this method, algae were suspended in a zinc solution. Aliquots of the solution were taken and zincon was added to the aliquots. The aliquots were taken in a manner which avoided the presence of algae particles in the aliquot.

Zincon has surprisingly been found to be particularly useful in the analysis of oral care compositions. It is believed that only free zinc (II) ions are therapeutically active (see U.S. Pat. No. 4,992,259). Zincon has been found to bind zinc weakly and therefore to provide a good estimate of the amount of free zinc (II) present. The presence of any materials which would render the zinc unavailable would prevent the zinc from reacting with the zincon.

In the present methods, the colour of the zincon indicator is monitored in situ as the oral care composition disperses into the solution. It has surprisingly been found that a colour change may be observed before the oral care composition disintegrates fully. The method may be used to compare metal ion release from different oral care compositions. The methods of Ejnik et al and Areco et al utilise detection by UV absorbance at a wavelength of 620 nm. Such methods are believed to be incompatible with the in situ analysis of oral care compositions during dispersion processes. Toothpastes, tooth powders and tooth gels comprise insoluble particulate materials. The presence of particulate materials causes light scattering, which interferes with UV/Vis spectroscopic detection. Light scattering appears in UV/Vis spectra as erroneously high absorbance values across a wide range of wavelengths. It is therefore incompatible with UV/Vis quantitation.

In some arrangements, the target metal ion is stannous. Zincon has surprisingly been found to react rapidly and selectively with stannous ions to produce a colourless complex. This is in contrast w earlier reports that zincon does not react with tin ions (Wilcox, 2009. "The black and white of immersion tin: keeping an eye on cupric ions can eliminate black tin", Printed Circuit Design & Fab, 1 Jul. 2009). The colourless complex also differs from the red-brown complex obtained electrochemically by Mabrouk et al (Mabrouk et al, 1992. "Direct electrochemical synthesis of cobalt, nickel, copper, zinc, cadmium, tin and lead zincon complexes", Trans. Met. Chem., 17, pp 1-4).

Zincon has been found to bind stannous ions more strongly than zinc ions. This allows for the detection of stannous ions even in the presence of zinc ions.

Notably, zincon does not appear to form a complex with stannic ions. The selective detection of stannous ions is important. This is because, unlike stannous ions, stannic ions are not believed to display useful therapeutic activity. Oxidising stannous ions to stannic ions reverses the formation of the stannous zincon complex, causing a colour change from colourless to red. In the presence of atmospheric oxygen, this oxidation reaction may occur spontaneously. Thus, the rate of oxidation of zincon in a solution may also be investigated. This allows the effects of additives and excipients present in the oral care composition on the oxidation of stannous ions to be investigated.

For some applications, it may be desirable to investigate the release of stannous ions separately from their oxidation. This may be achieved by conducting step (ii) of the method in an inert gas atmosphere. Useful inert gases include nitrogen and argon.

The susceptibility of stannous ions to oxidation may be exploited to allow the detection of the release of zinc ions from a composition further comprising stannous ions. This is achieved by including in the solution an oxidising agent. The oxidising agent oxidises the stannous ions to stannic ions, thereby allowing the zinc ions to react with the zincon.

An alternative method for detecting the release of zinc ions from a composition comprising a source of stannous ions simply involves the use of an increased concentration of zincon. Any zincon not bound to stannous will be available for reaction with zinc.

In the arrangement where zinc is the target ion and the sample comprises a source of stannous ions, it is preferable to make use of an oxidising agent. Examples of oxidizing agents useful in the present methods include peroxides such as hydrogen peroxide; peracetic acid; persulfates such as sodium persulfate and potassium persulfate; hypochlorites such as sodium hypochlorite; chlorates; perchlorates; iodates; periodates; bromates; perbromates; iodine; and bromine.

Hydrogen peroxide is a preferred oxidising agent. Hydrogen peroxide is widely available commercially. The hydrogen peroxide may be supplied in an aqueous solution, for example an aqueous solution comprising hydrogen peroxide in an amount in the range of 1 to 5% by weight. Dilute aqueous solutions of hydrogen peroxide are less hazardous than concentrated solutions, and generally have adequate oxidising power.

The methods described herein include the step of providing a solution comprising an indicator having a colour.

The indicator comprises zincon. Zincon is an ionizable compound. Zincon may therefore be provided in the form of a salt. The counterion present in the salt is selected such that the counterion does not interfere with the detection of zinc ions. Suitable salts may be identified for example by contacting the salt with a solution known to contain zinc (II) ions. If a blue complex is formed, then the cotmterion is suitable. A preferred salt is zincon monosodium, which is commercially available.

In the arrangements where the indicator is in the form of a solution, the amount of zincon present in the indicator preferably does not exceed 100 ppm. For example, zincon may be present in the indicator in an amount in the range of 10 to 100 ppm, optionally 10 to 60 ppm or 20 to 60 ppm. By providing a dilute indicator solution, the sensitivity of the method is improved because a lower concentration of the target metal ion is required to produce an observable colour change.

The solution comprises a solvent. The solvent is most preferably water, in order to model more closely the conditions in the oral cavity. Other solvents may be used. However, it should be noted that zincon is poorly soluble in many organic solvents. The use of co-solvent mixtures, for example ethanol/water, is contemplated herein. The pH of the solution may be in the range of 7 to 10, or preferably 9 to 9.5. Zincon has acidic functional groups which become ionized at alkaline pH. Providing a solution which is mildly alkaline therefore assists in dissolving the zincon and facilitates the reaction of zincon with positively-charged metal ions. A pH in the range of 9 to 9.5 is particularly advantageous in the arrangements where the target metal ion is zinc (II). This is because pH has a greater impact on the reaction of zinc with zincon than on the reaction of stannous with zincon.

The solution may comprise a buffer for maintaining the pH within the desired range. One of skill in the art will be familiar with buffer solutions. The buffer preferably does not comprise a chelating agent, particularly in the arrangements where the target metal ion is zinc (II). Zinc ions are bound by zincon weakly, and the presence of chelating agents may therefore interfere with their detection. Weak chelating agents, i.e. those chelating agents which bind to zinc less strongly than zincon, are tolerated. Such chelating agents may be readily identified by contacting a solution of zincon zinc with the chelating agent. Any colour change from blue to red, indicating the loss of zincon zinc, would show that the chelating agent is unsuitable. Stannous binds zincon strongly, and a broad range of chelating agents are tolerated in the arrangements where the target metal ion is stannous.

The buffer may be an ammonia buffer. The ammonia buffer may be present in the solution at a concentration in the range 0.02 to 5 M; and optionally at a concentration of 0.1 M. The butler may be a borate buffer. Borate buffers and ammonia buffers are useful in solutions having a pH in the range 8.5 to 9.5. The buffer may be HEPES, optionally at a concentration in the range 0.1 to 1 M. HEPES is useful in solutions having a pH of approximately 7. The buffer may be TRIS (available from Sigma-Aldrich under the trade name TRIZMA®), optionally at a concentration of 0.1 to 1 M. TRIS is useful in solutions having a pH in the range 7 to 8.5. Other buffers may be used.

The temperature of the solution is most advantageously room temperature (21 to 27° C., or 25° C.). Dispersion of the oral care composition at room temperature is generally slower than at higher temperatures, allowing for the more straightforward measurement of the rate of release of the metal ions.

The methods provided herein include dispersing a sample comprising at least one source of the target metal ion into the solution.

The sample is an oral care composition selected from a toothpaste, a tooth gel, and a tooth powder. The oral care composition is preferably a toothpaste or a tooth gel. The skilled artisan will be familiar with the formulation of such compositions, and the specific nature of the components used is not particularly limited.

For example, the oral care composition may comprise one or more ingredients selected from abrasives, oral care actives, such as anti-caries agents and anti-calculus agents; nutrients, such as vitamins; polymers; enzymes; humectants; thickeners; viscosity modifiers; antimicrobial agents; chelating agents; pH adjusting agents; preservatives; flavorings; sweeteners; whitening agents, colorants, herbal extracts and combinations thereof.

Preferably, the oral care composition is substantially free of colourants. This allows the colour change of the indicator to be observed more easily. However, the presence of colourants is tolerated because free zincon is strongly coloured. This means that the colour change of the zincon indicator is detectable even if a background colour is present.

The oral care composition preferably comprises at least one water insoluble material. As used herein, "water insoluble" refers to materials having a solubility of 0.01 mg/ml or less in deionised water at 25° C. Suitable materials are known as abrasives, for example, silica and calcium carbonate. The oral care composition may comprise at least 50%, and preferably at least 75 water insoluble material by weight of the composition. Alternatively or additionally, the oral care composition may comprise a gel phase. Gels and insoluble materials disperse slowly in water, making the compositions well suited for use in the present methods.

The sample comprises at least one source of the target metal ions.

Examples of sources of zinc ions include zinc acetate, zinc acetylacetonate, zinc ammonium sulfate, zinc benzoate, zinc bromide, zinc borate, zinc butylphthalate, zinc butylxanthate, zinc caprylate, zinc carbonate, zinc chloroanilate, zinc, citrate, zinc cyclohexanebutyrate, zinc chloride, zinc gallate, zinc fluoride, zinc alpha-glucoheptonate, zinc gluconate, zinc glycerophosphate, zinc hydroxide, zinc 12-hydroxystearate, zinc iodide, zinc acrylate, zinc oxide, zinc propionate, zinc isovalerate, zinc D-lactate, zinc DL-lactate zinc laurite, zinc hexafluorosilicate, zinc methacrylate, zinc molybdate, zinc napthenate, zinc octoate, zinc oleate, zinc orthophosphate, zinc phenolsulfonate, zinc pyridine-2thiol-1-oxide, zinc pyrophosphate, zinc resinate, zinc saucy late, zinc sulfate, zinc nitrate, zinc selenide, zinc stearate, zinc sulfanilate, zinc tartrate, zinc tellurate, zinc tungstate, zinc valerate, zinc vanadate, and zinc tribromosalicylanilide. Other sources of zinc ions may be used.

Examples of sources of stannous ions include stannous fluoride, stannous chloride, stannous acetate, stannous gluconate, stannous oxalate, stannous sulfate, stannous lactate and stannous tartrate. Other sources of stannous ions may be used.

The oral care composition may comprise both a source of stannous ions and a source of zinc ions. In this arrangement, the target metal ion is selected by adjusting the composition of the solution. If the solution comprises an oxidising agent, or if a high concentration of Zincon is used then the target metal ion is zinc. Otherwise, the target metal ion is stannous, because stannous binds to zincon more strongly than it does to zinc.

The method includes the step of dispersing the sample into the solution.

This step generally comprises mixing or agitating the solution. This may be achieved through the use of, for example, an orbital shaker. Alternatively, the solution may simply be allowed to disperse by diffusion into the solution.

The rate of release of metal ions will vary with the amount of mixing or agitating. Advantageously, the rate is suitably selected such that the sample remains partially intact throughout the duration of the experiment i.e. such that the sample is not fully dispersed. Dispersing the sample only partially limits the rate of release of the metal ions, thereby making the rate easier to observe.

Suitably, the same method of dispersion and dispersion conditions is used for each in order to allow for the more reliable comparison of the rates of release of metal ions from the compositions.

The method includes, during step (ii), monitoring the colour of the indicator to determine the rate of release of the target metal ion from the sample.

Monitoring the colour of the indicator generally involves the simple visual observation of the solution. In this arrangement, a qualitative estimate of the rate of release of the target metal ion from the sample is obtained.

The present methods are particularly useful for the side by side comparison of two or more samples. The samples are suitably different from one another. The samples may be oral care compositions having different formulations or obtained by different manufacturing methods. The samples may have different ages. For example, a newly manufactured composition may be compared with a composition which has been stored for an extended period, such as at least 6 months or at least 12 months, or at least 18 months. This would allow any changes in metal release properties to be investigated, e.g. for the purposes of estimating shelf life.

Step (iii) of the methods described herein may comprise recording a video of the solution. This may be achieved using a digital video camera or any other appropriate device. Videos are useful for allowing the comparison of different oral care compositions without the need to test all of the compositions simultaneously.

The video data may be stored in an electronic retrieval system, for example a database or a computer file system.

Further provided herein is the use of an indicator to measure the rate of release of a target metal ion from an oral care composition into a solution, wherein the target metal ion is selected from stannous and zinc (II), wherein the oral care composition is selected from a toothpaste, a tooth gel, and a tooth powder, and wherein the indicator comprises zincon. The use may he in a method as described above. The target metal ion may he zinc (II). In this arrangement, the oral care composition may further comprise a source of stannous ions and the solution may comprise an oxidising agent. The oxidising agent oxidises the stannous ions to stannic ions thereby allowing the zincon to react with the zinc.

Alternatively, the target metal ion is stannous. In this arrangement, the use may further comprise using the indicator to detect the rate of oxidation of the stannous ions. Typically, the oxidation is the result of exposure of the stannous ions to oxygen in the atmosphere.

EXAMPLES

The present invention will now be explained by reference to the following non-limiting examples.

Example 1

Method for Detecting Stannous Ion Release

An illustrative method for detecting the rate of release of stannous ions from an oral care composition is set out below. The method allows a straightforward qualitative determination of the relative rate of release of stannous ions from an oral care composition. The method is particularly useful for side-by-side comparison of a series of oral care compositions.

The method is as follows:

1. Prepare an indicator solution comprising 40 ppm zincon sodium salt in a 0.2 M ammonia buffer at a pH in the range 9 to 9.5.

2. Add approximately 0.5 g of a toothpaste sample into a 20 mL scintillation vial. Place the vial on to an orbital shaker against a light coloured background.

3. Add 2 to 3 mL of the zincon solution into the vial. Start the orbital shaker. A slow shaking speed should be selected.

4. Observe the indicator. The rate of the disappearance of the colour of the indicator correlates with the rate of release of the stannous ions.

5. When the indicator has turned colourless, stop the orbital shaker. Allow the samples to stand in air for approximately 5 minutes. Inspect the sample. If the rate of oxidation of the stannous ions to stannic ions by oxygen in the atmosphere exceeds the rate of release of stannous ions from the toothpaste, the solution will undergo a colour change from colourless to blue or red.

Accordingly, the present method allows the determination of the rate of release of stannous ions and the rate of oxidation of stannous ions to stannic ions. The method is useful in the analysis of oral care compositions, for example when formulating new oral care compositions.

Example 2

Detecting the Rate of Release of Zinc Ions from a Composition Comprising Zinc Ions and Stannous Ions Oral care compositions n ay comprise both zinc ions and stannous ions. Zincon binds stannous ions in preference to zinc ions. However, by adjusting the composition of the solution into which the oral care composition is dispersed, the release of zinc ions from a composition comprising both zinc ions and stannous ions may be detected. An illustrative method of detecting the rate of release of zinc ions is as follows:

1. Prepare a zincon solution as described in Example 1.
2. Add about 0.5 g of a toothpaste sample into a 20 mL scintillation vial. Place the vial on an orbital shaker against a light background, such as white paper.
3. Add 100 µL of an aqueous solution comprising hydrogen peroxide in an amount of 3% by weight to 3 mL of the zincon solution.
4. Add the resulting mixture to the vial and start the orbital shaker. Select a slow shaking speed such that the toothpaste remains essentially intact.
5. Observe the colour of the solution. The rate of the colour change from red to blue correlates with the rate of the release of zinc from the toothpaste. If the solution undergoes a colour change to colourless, then the stannous ion has not been fully oxidised. The concentrations of hydrogen peroxide and/or zincon dye may be increased in this event.

Accordingly, the present methods allow the detection of the release of zinc from oral care compositions comprising both zinc and stannous ions.

What is claimed is:

1. A method of measuring the relative rates of release of a target metal ion from two or more samples, each sample comprising at least one source of the target metal ion, which method comprises:
    (i) providing at least two aliquots of a solution including an indicator, the indicator having a colour;
    (ii) dispersing each sample into one of the aliquots; and
    (iii) during step (ii), monitoring the colour of the indicator in situ to determine the rates of release of the target metal ion from the samples relative to one another;
    wherein the indicator comprises zincon;
    wherein each sample is an oral care composition selected from a toothpaste, a tooth gel, and a tooth powder; and
    wherein the target metal ion is selected from stannous or stannous and zinc (II) in combination.

2. The method of claim 1, wherein the solution has a pH in the range of 7 to 10.

3. The method of claim 2, wherein the solution has a pH in the range 9 to 9.5.

4. The method of claim 1, wherein the solution comprises a buffer.

5. The method of claim 1, wherein the zincon is present in the solution in an amount in the range 10 to 100 ppm.

6. The method of claim 1, wherein the temperature of the solution is in the range 21 ° C. to 27 ° C.

7. The method of claim 1, wherein step (iii) comprises recording a video of the aliquots.

8. The method of claim 1, wherein each sample further comprises a source of zinc ions.

9. The method of claim 1, wherein step (ii) comprises agitating the aliquots in the presence of oxygen, the agitation being intermittent so as to allow oxidation of stannous ions to be detected using the indicator.

10. The method of claim 1, wherein the target metal ion is zinc (II), wherein each sample further comprises a source of stannous ions, and wherein the solution includes an oxidizing agent for oxidizing the stannous ions to stannic ions.

* * * * *